United States Patent [19]

Dennis et al.

[11] Patent Number: 4,857,102

[45] Date of Patent: Aug. 15, 1989

[54] ALDITOL ESTER DERIVATIVE OF TRICLOPYR, AND HERBICIDAL USE THEREOF

[75] Inventors: Nicholas Dennis, King's Lynn; Donald C. Burrell, Newbury, both of England

[73] Assignee: The Dow Chemical Company, Midland, Mich.

[21] Appl. No.: 36,947

[22] Filed: Apr. 10, 1987

[30] Foreign Application Priority Data

May 28, 1986 [GB] United Kingdom ................ 8612940

[51] Int. Cl.$^4$ ................ C07D 401/12; C07D 401/14; A01N 43/40

[52] U.S. Cl. ...................................... 71/94; 546/256; 546/270; 546/283

[58] Field of Search ................ 546/270, 256, 283; 71/94

[56] References Cited

PUBLICATIONS

Lewer et al., Chemical Abstracts, vol. 108(17), abst. No. 108:145,339a, Apr. 25, 1988.

*Primary Examiner*—Alan L. Rotman
*Attorney, Agent, or Firm*—S. Preston Jones; Ronald G. Brookens

[57] ABSTRACT

Alditol ester derivatives of triclopyr are prepared and used as postemergent herbicides in cereal grain crop areas to kill and control various weeds.

48 Claims, No Drawings

ALDITOL ESTER DERIVATIVE OF TRICLOPYR, AND HERBICIDAL USE THEREOF

BACKGROUND OF THE INVENTION

The compound 3,5,6-trichloro-2-pyridyloxy acetic acid, having the common name triclopyr, is a commercial herbicide employed to kill and control various weeds and grasses. Triclopyr is also known to cause phytotoxic damage to cereal grains such as wheat, barley and rice when applied postemergently in a herbicidally effective amount upon weeds commonly encountered in cereal grain crop areas. The compound is also sufficiently volatile to warrant concern for susceptible valuable crops when applied to adjacent land.

It is therefore desirable to find ways to reduce the unwanted phytotoxicity of the compound thereby increasing its value for use in the presence of cereal grain crops.

SUMMARY OF THE INVENTION

The present invention provides alditol ester derivative of triclopyr corresponding to one of the following general formulae:

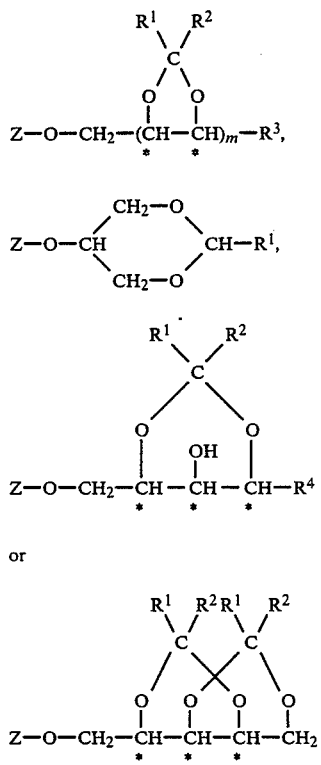

wherein
Z represents

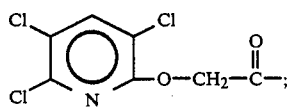

$R^1$ and $R^2$ are each independently any sterically compatible combination of H, a $C_1$–$C_6$ straight chain or branched alkyl group, a $C_3$–$C_6$ cycloalkyl group, or phenyl;

$R^1$ and $R^2$ taken together represent a divalent polymethylene group $-(CH_2)_n-$, thereby forming a carbocyclic ring having n+1 carbon atoms wherein n is 3, 4, 5 or 6;

$R^3$ is H or a group of the formula:

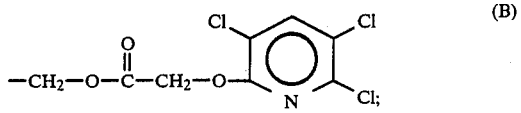

$R^4$ is H, $CH_2OH$ or a group of formula B; and m is 1 or 2.

The term halogen is meant any of Br, Cl, F, or I, although Br and Cl are preferred.

The compounds of the general formulae I, III and IV contain one or more asymmetric carbon atoms, indicated as * in the formulae given above.

Thus, the compounds of the invention, having chiral groups, occur as optical isomers and in some cases, they also exist in the form of geometrical isomers. Accordingly, the invention also provides for the individual isomers as well as mixtures thereof and it should be understood that the written nomenclature and structural formulae shown in the present specification should be taken to include the individual isomers as well as mixtures thereof.

Compounds of the general formulae I, II, III and IV having substantially lower volatility than triclopyr and having useful herbicidal activity against one or more significant broad leaf weeds such as fat hen (Chenopodium album) or red dead nettle (Lamium purpureum). The compounds are thus useful in controlling such weeds in land adjacent valuable susceptible crops.

Compounds of the general formulae I to IV wherein $R^1$ and $R^2$ are each independently H, $CH_3$, phenyl or phenyl substituted with one or two halogen, lower alkyl, lower alkoxy, lower alkylthio, nitro and/or dialkylamino groups; m is 1 or 2; $R^3$ is H or a group of formulae B and $R^4$ is as defined above exhibit useful herbicidal activity against one or more significant broad leaf weeds, such as fat hen (Chenopodium album) or red dead nettle (Lamium purpureum). In some instances the instant compounds have herbicidal activity equal to or greater than triclopyr or its commercially available ester or sodium or amine salts, while exhibiting excellent tolerance by cereal grains particularly wheat, barley and rice.

Of the compounds according to the invention, those prepared from the acetal of glycerol or from the acetonides of the pentitols, arabitol, adonitol and xylitol are of particular interest, more particularly those prepared from acetonides of arabitol and xylitol.

There should be mentioned especially those compounds in which $R^1$ and $R^2$ are the same or different and each represents H, $CH_3$ or phenyl. More especially are those compouns in which $R^1$ and $R^2$ are each H or methyl groups, or in which $R^1$ is H and $R^2$ is phenyl. Preferably, $R^1$ and $R^2$ are either identical, or else $R^1$ is hydrogen.

Examples of specific compounds having an excellent herbicidal action toward the weeds, fat hen and/or red dead nettle in addition to excellent cereal grain tolerance at herbicidally effective dosage rates for the susceptible noxious weeds of the type described, include

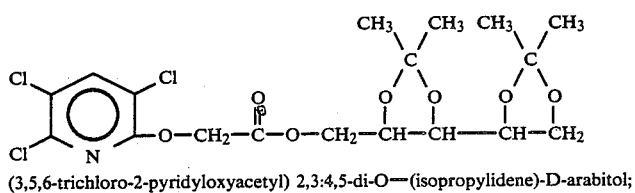
(3,5,6-trichloro-2-pyridyloxyacetyl) 2,3:4,5-di-O—(isopropylidene)-D-arabitol; (V)

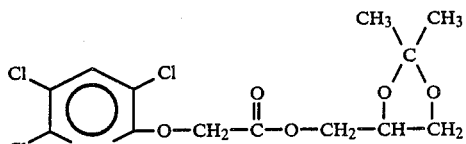
(3,5,6-trichloro-2-pyridyloxyacetyl) 1,2-(isopropylidene)-glycerol; (VI)

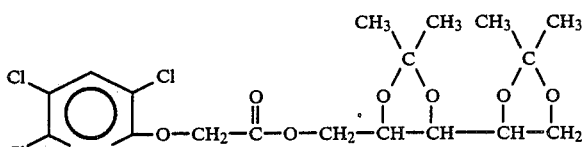
(3,5,6-trichloro-2-pyridyloxyacetyl) 2,3:4,5-di-O—(isopropylidene)-xylitol; (VII)

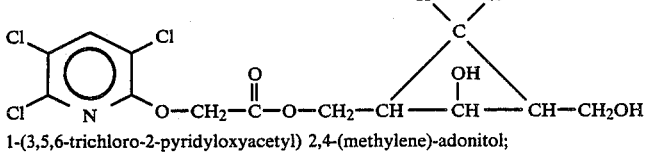
1-(3,5,6-trichloro-2-pyridyloxyacetyl) 2,4-(methylene)-adonitol; (VIII)

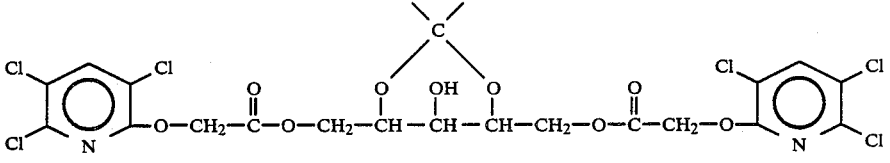
bis-[1,5-(3,5,6-trichloro-2-pyridyloxyacetyl)] 2,4-(methylene)-adonitol; (IX)

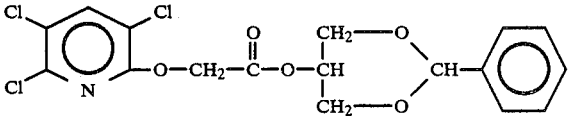
(3,5,6-trichloro-2-pyridyloxyacetyl) 1,3-benzylidene glycerol; (X)

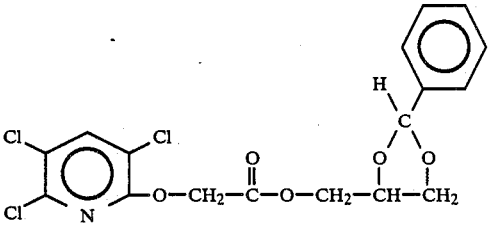
(3,5,6-trichloro-2-pyridyloxyacetyl) 1,2-(benzylidene)-glycerol; (XI)

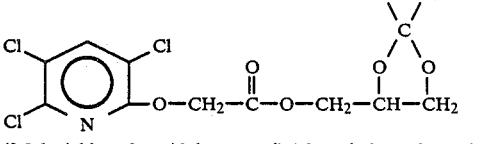
(3,5,6-trichloro-2-pyridyloxyacetyl) 1,2-methylene glycerol; and (XII)

-continued

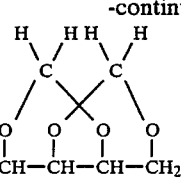
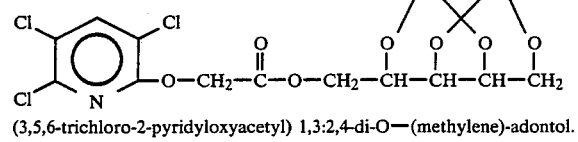
(XIII)

(3,5,6-trichloro-2-pyridyloxyacetyl) 1,3:2,4-di-O—(methylene)-adontol.

Compounds V, VI, VII and VIII are most preferred on account of their herbicidal activity and broader spectrum.

Examples of compounds in accordance with the invention, which are not as selective as compounds to XIII above, but which nevertheless have significant herbicidal activity and low volatility are the following:

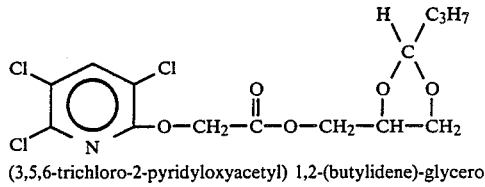

(3,5,6-trichloro-2-pyridyloxyacetyl) 1,2-(butylidene)-glycerol;

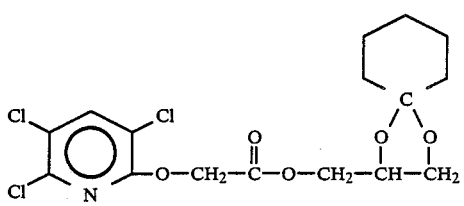

(3,5,6-trichloro-2-pyridyloxyacetyl) 1,2-(cyclohexylidene)-glycerol;

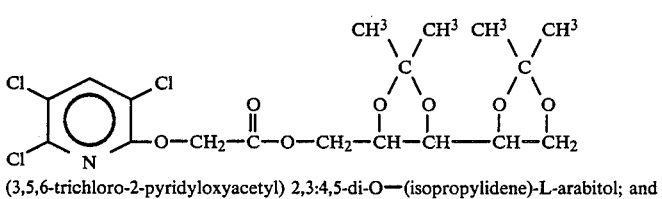

(3,5,6-trichloro-2-pyridyloxyacetyl) 2,3:4,5-di-O—(isopropylidene)-L-arabitol; and

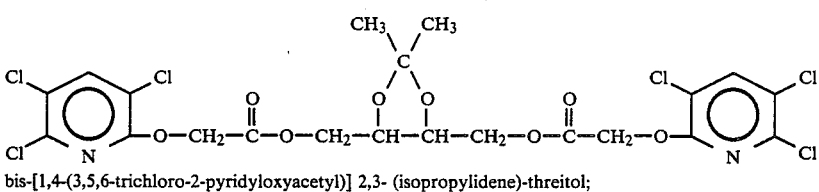

bis-[1,4-(3,5,6-trichloro-2-pyridyloxyacetyl)] 2,3- (isopropylidene)-threitol;

It will be noted that certain of the above compounds, for example, compounds V, VII and XVI, appear from the structural formulae given to be identical. These compounds, however, are different because they differ in their stereochemistry.

The compounds of the present invention may be prepared by the reaction of a compound of the formula

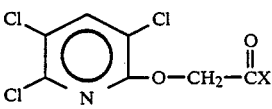

wherein X is hydroxy, halogen or the residue of $C_1$-$C_6$ aliphatic alcohol with a compound of the formula $$HO-R^5$$

wherein $R^5$ is one of the general formulae (C)

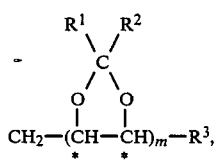

(D)

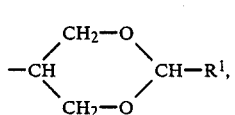

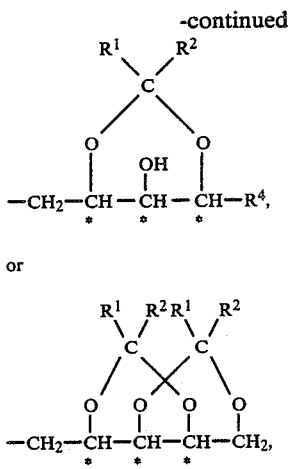

In particular, when the starting material is trichlopyr itself, i.e., X is hydroxy, the reaction may preferably be carried out at room temperature in an inert polar solvent, such as tetrahydrofuran, or acetonitrile in the presence of a coupling agent such as N,N'-carbonyldiimidazole, or dicyclohexylcarbodiimide.

The solvent is preferably dried before use, for example, using a molecular sieve such as Aldrich type 3A or 4A.

The reaction of the acid halide of triclopyr (i.e., wherein X is halogen) with the alditol derivative may be carried out at a temperature of from about room temperature up to about 100° C. or more. The reaction is also carried out in a solvent such as acetonitrile, tetrahydrofuran, or dimethylsulfoxide and in the presence of an acid binding agent or scavenger (acid acceptor) such as dimethylamine, triethylamine, piperidine, pyridine, 4-dimethylaminopyridine, sodium carbonate, or potassium carbonate to achieve the desired condensation. The reaction product may then be filtered to remove any salt produced, for example, the amine hydrochloride salt produced when the scavenger used is an amine.

The acid halide of triclopyr may be prepared by the reaction of triclopyr with a suitable halogenating agent, such as $SOCl_2$ or $POCl_3$, in an inert aprotic solvent medium such as toluene, benzene or carbon tetrachloride and under convention acid halide formation conditions to form the acid chloride or other acid halide.

When the starting material is an ester of triclopyr (i.e., X is the residue of a $C_1$-$C_6$ alcohol), the reaction is a transesterification reaction, and is preferably carried out in an aprotic solvent medium in the presence of p-toluenesulphonic acid. The preferred ester reactant is the methyl ester. After the completion of the reaction, the solvent may then be removed leaving the desired product as a residue.

Accordingly, the present invention provides a process for the preparation of a compound of the general formulae I, II, III or IV above by any of the processes described above.

The starting materials of the formula HO—$R^5$ wherein $R^5$ is as hereinabove defined may be prepared from the requisite alditol (polyhydroxyalcohol) and an appropriate aldehyde or ketone in the following manner:

The selected ketone or aldehyde and the alditol are brought together in a molar ratio in excess of 2:1 wherein it is anticipated that one dioxo ring will be formed, or 4:1 wherrein it is expected two dioxo rings will be formed, and in the presence of a small amount of each of copper sulphate and concentrated sulfuric acid and the mixture is stirred, conveniently at room temperature, for from about 5 to about 24 hours or until the reaction is complete. The aldehyde or ketone is preferably used in substantial excess; the aldehyde or ketone, for example, may be used in a sufficient excess so as to act as a reactant and as the reaction solvent. The mixture is then neutralized, for example, with aqueous ammonia. The copper sulphate and any other insoluble solids are filtered off, after which the reaction mixture can be concentrated employing conventional procedures. In one such procedure a rotary evaporator can be employed. The crude residue can be purified employing conventional procedures. Most of the compounds can be recovered, for example, by distillation in a khugelrohr apparatus, generally yielding the product as a oil.

Alternatively, the alditol may be reacted with the aldehyde or ketone in the presence of a suitable ion exchange resin, e.g. "DOWEX 50X8-400" (DOWEX is a Trade Mark of The Dow Chemical Company).

Suitable ketones for condensation with the alditol include acetone or diisopropylketone or other ketones of the structure:

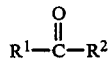

wherein $R^1$ and $R^2$ are as defined above.

Suitable aldehydes are formaldehyde, acetaldehyde, butyraldehyde, benzaldehyde, and chloral.

When the alditol derivative has two free hydroxyl groups (compounds of formulae C or E), either mono or bis addition of the trichlopyr (or its derivative) is possible. By adding the trichlopyr (or its derivative) reactant to the alditol derivative reactant, rather than the reverse, and controlling the amount of the reactant added to the stoichiometric amount, it is possible to arrange for substantially 1:1 addition, and thereby to prepare the compounds of the invention of formula III, wherein $R^4$ is $CH_2OH$. Further addition gives the bis-substituted product (where $R^4$ is the group of formula A).

The compounds of the invention may be isolated from the reaction mixture by customary processes, for example, by distilling off the solvent used at normal or reduced pressure, by precipitation with water or by extraction. Generally, a higher degree of purity can be obtained by purification by conventional column-chromatography or flash chromatography, or recrystallization of the product if a solid.

The compounds according to the invention are generally a yellowish gum in character, but some are non-crystalline solids, and some are crystalline solids that are insoluble in water, and to a limited extent, in aliphatic hydrocarbons, such as, for example, petroleum ether, hexane, pentane and cyclohexane; and readily soluble in halogenated hydrocarbons, such as, for example, chloroform, methylene chloride and carbon tetrachloride, aromatic hydrocarbons, such as, for example, benzene, toluene and xylene, ethers, such as, for example, diethyl ether, tetrahydrofuran and dioxan, carboxylic acid nitriles, such as, for example, acetonitrile, ketones, such as, for example, acetone, alcohols, such as, for example, methanol and ethanol, carboxylic acid amides, such as, for example, dimethylformamide, and sulphoxides, such as, for example, dimethyl sulphoxide.

During the synthesis, the active compounds are generally obtained as a racemic mixture and can be separated into the optical isomers utilizing known procedures, for example, fractional crystallization can be employed if the compound is a solid, or using a chiral chromatographic column or by reacting with a resolving agent such as an alkaloid such as brucine.

Synthesis of the optically pure compounds in accordance with the invention may be carried out by using an optically unambiguous D or L alditol as the starting material in making the alditol derivative.

The optical isomers, or enantiomers, of the compounds of the invention exhibit differing biological activity, although neither the D or L form consistently has the greater herbicidal action nor marked difference in selectivity and weed spectrum. The activity of the different isomer can be easily observed.

The starting materials for the preparation of the compounds of the invention are all known compounds and can be obtained commercially or manufactured according to known procedures.

The compounds of the invention may be used alone or in a mixture with one another or the compounds can be employed along with other active substances, such as, for example, defoliants, plant protecting agents and/or pesticides depending on the desired purpose.

The specific compound or mixture of compounds of the present invention to be employed are not the same for all weeds and all crop plants, and are dependent on the specific weed species to be controlled and the specific crop plant present.

If a broadening of the spectrum of action is intended, other biocides may also be employed. Examples of suitable herbicidally active mixing partners are carbamic acid derivatives such as phenmedipham, triallate, diallate, and vernolate; dinitrophenol derivatives such as dinoseb and dinoseb acetate; chlorinated aliphatic acids such as trichloroacetic acid and dalapon; amides such as diphenamid and N,N-diallyl-2,2-chloroacetamide; dipyridilium compounds such as paraquat and diquat; anilides such as propanil, solan, monalide, propachlor, 2-chloro-2',6'-diethyl-N-methoxymethylacetanlide; nitriles such as dichlobenil and ioxynil; urea derivatives such as linuron, chloroxuron, monolinuron, fluometuron and diuron; triazine derivatives such as simazine, atrazine, ametryn, prometryn, desmetryn, methoprotryn, cyanazine and terbumeton; uracil derivatives such as lenacil and bromacil; growth-promoting preparations such as (2,4,5-trichlorophenoxy)acetic acid, 4-(4-chloro-2-methylphenoxy)butyric acid. 2,3,6-trichlorobenzoic acid, 2-(4-chloro-2-methylphenoxy)-propanoic acid and 3,6-dichloro-2-methoxybenzoic acid; aryloxy phenoxy postemergence grass killers, such as haloxyfop; pyridine derivatives such as picloram, clopyralid and fluoroxypyr; and other preparations such as flurecol, 3,4-dichloropropionanilide, trifluralin, bensulide, bifenox, bentazone, pyridate and glyphosate.

Particularly suitable mixing partners are the following: propanil, dichlobenil, ioxynil, diuron, atrazine, cyanazine, bromacil, (2,4,5-trichlorophenoxy)acetic acid, 2,3,6-trichlorobenzoic acid, 2-(N-chloro-2-methylphenoxy)propanoic acid, 3,6-dichloro-2-methoxybenzoic acid, picloram, clopyralid, fluoroxypyr, bentazone, pyridate and glyphosate.

Surprisingly, mixtures, according to the invention, exhibit a considerably increased action against weeds with little, if any, damage to the cereal grains treated therewith. Used together with compounds of the invention, the herbicidal action of the mixing partners mentioned is such that, under difficult conditions, such as application in high quantities, they have no specific damaging effect on cereal grains while at the same time their spectrum of action against the weed type is broadened.

The ratio of the components in the mixtures according to the invention is preferably approximately from 1:10 to 10:1 more especially from 1:3 to 3:1 by weight.

The exact dosage to be employed is not the same for all plants with all compounds and is dependent upon the plant species and the stage of growth at which treatment is made, and climatic conditions such as temperature, wind, and especially rainfall.

Preferred application quantities for selective weed control range from 0.5 to 5.0 kg/ha for the mixing partners listed and from 0.2 to 2 kg/ha for the compounds in accordance with the invention.

It is also advantageous to apply from 0.25 to 5.0 kg/ha of a suitable surface-active substance and other agents that intensify action, for example, non-phytotoxic oils.

Advantageously, the active agents, materials or substances according to the invention or mixtures thereof are used in the form of preparations, for example, powders, strewable agents, granulates, solutions, emulsions or suspensions, with the addition of liquid and/or solid carriers or diluents and, if desired, wetting agents, adhesion-promoting agents, emulsifiers and/or dispersing agents, but preferably in the form of emulsion and emulsifiable concentrates.

Accordingly, the present invention provides a herbicidal preparation which comprises at least one compound of the general formulae I, II, III or IV, or a mixture thereof, and a suitable liquid or solid carrier.

Suitable liquid carriers are, for example, water, aliphatic and aromatic hydrocarbons, such as, for example, toluene and xylene, cyclohexanone, isophorone, dimethyl sulphoxide, dimethylformamide, and also mineral oil fractions.

Suitable solid carriers are, for example, mineral earths, for example, tonsil, silica gel, talcum, kaolin, attaclay, limestone, silica acid and vegetable products, for example, meals.

The preparation advantageously includes a surface-active substance(s). Suitable surface-active substances are, for example, calcium ligninsulphonate, polyoxyethylene alkylphenol ethers, naphthalenesulphonic acids and salts thereof, phenolsulphonic acids and salts thereof, formaldehyde condensates, fatty alcohol sulphates and substituted benzenesulphonic acids and salts thereof.

The proportion of the active substances in the various preparations may vary within wide limits. For example, the preparations may contain from 5 to 95 percent by weight of active substances, from 95 to 5 percent by weight of liquid or solid carriers and, if desired, up to 20 percent by weight of surface-active substances.

The present invention also provides a process of combating weeds, which comprises applying postemergently to said weeds, a compound or mixture of compounds in accordance with the invention; and if desired, other active substances, especially an additional herbicide from the list of mixing partners given hereinabove.

Suitably, the compounds are in the form of a herbicidal preparation comprising the active ingredient and carrier and herbicide mixing partner when one is used.

The compounds or preparations may be applied in customary manner, for example, using water as a carrier. The final preparations may be employed in quantities of spraying liquor of from 100 to 1000 liters/ha. It is possible to use the active agents in the so-called Low Volume and Ultra Low Volume processes, and also to apply them in the form of so-called micro-granules.

The following examples illustrate the present invention and the manner in which it can be practiced but as such, are not to be construed as limitations upon the overall scope of the same.

EXAMPLE 1

A. 2,3:4,5-Di-isopropylidene-L-arabitol

A mixture of L-(−)-arabitol (30 g, 0.197 mole) anhydrous copper sulphate (24 g), concentrated sulphuric acid (4 ml) and acetone (600 ml) were stirred well at room temperature for 18 hours, then neutralized with concentrated aqueous ammonia and filtered. The solution was concentrated using a rotary evaporator to yield a yellow oil as residue. The yellow oil was distilled on a khugelrohr apparatus (110° C.) to yield the title compound (35.5 g, 78 percent) as a colorless oil.

Elemental Analysis

|  | C | H |
|---|---|---|
| Calculated for $C_{11}H_{20}O_5$: | 56.88 | 8.68 |
| Found: | 56.87 | 8.52 |

B. 3,5,6-Trichloro-2-pyridyloxyacetyl Chloride (Acid Chloride of Triclopyr)

3,5,6-Trichloro-2-pyridyloxyacetic acid (20 g, 0.078 mole was stirred with toluene (46.5 ml). Thionyl chloride (26 ml) was added dropwise to the well-stirred mixture over 15 minutes. The mixture was then heated under reflux (70° C.) for 3 hours. The effluent gases ($SO_2$+HCl) were absorbed into aqueous 5N sodium hydroxide. The cooled reaction mixture was filtered and evaporated to yield the title compound (20.9 g, 98 percent) as a thick dark brown oil.

C. (3,5,6-Trichloro-2-pyridyloxyacetyl)-2,3:4,5-di-O-(isopropylidene)-L-arabitol (Compound XVI)

2.3:4,5-Di-O-isopropylidene-L-arabitol (6 g, 0.026 mole) was dissolved in acetonitrile (30 ml) and triethylamine (3 g) added. 3,5,6-Trichloro-2-pyridyloxyacetyl chloride (7.1 g, 0.026 mole, in acetonitrile (20 ml) was added dropwise with stirring over 15-20 minutes. The mixture was stirred for an additional 3 hours, and the completion of the reaction was determined employing thin layer chromatography (TLC) of small samples of the reaction mixture.

On cooling, the solid precipitate was removed by filtration, and the filtrate concentrated employing a rotary evaporator. The oily residue was taken up in dichloromethane (100 mls) and washed thoroughly with water to remove any triethylamine hydrochloride remaining. After drying with sodium sulphate, evaporation of the dichloromethane layer gave a thick dark brown oil as a crude product.

This was eluted over a neutral alumina column using benzene as the solvent to yield the title compound (6.9 g, 57 percent) as a pale yellow viscous gum.

Elemental Analysis

|  | C | H | N |
|---|---|---|---|
| Calculated for $C_{18}H_{22}Cl_3NO_7$: | 45.93 | 4.71 | 2.98 |
| Found: | 46.10 | 4.55 | 2.98 |

EXAMPLE 2

A. 2,3:4,5-Di-O-isopropylidene-D-arabitol

A mixture of D-(+)-arabitol (30 g, 0.197 mole) anhydrous copper sulphate (24 g), concentrated sulphuric acid (4 ml), and acetone (600 ml) were stirred well at room temperature for 18 hours, then neutralized with concentrated aqueous ammonia and filtered. The solution was concentrated using a rotary evaporator to yield a blue-green oil as the residue.

The blue-green oil was distilled on a khugelrohr apparatus (110° C.) to yield the title compound (38.0 g, 83 percent) as a colorless oil.

B. 3,5,6-Trichloro-2-pyridyloxyacetyl-2,3:4,5-di-O-(isopropylidene)-D-arabitol (Compound V)

The procedure of Example 1-C was repeated except there was used the above described 2,3:4,5-di-O-isopropylidene-L-arabitol in place of the D compound.

The title compound was obtained (8.3 g, 68 percent) as a pale yellow viscous gum.

Elemental Analysis

|  | C | H | N |
|---|---|---|---|
| Calculated for $C_{18}H_{22}Cl_3NO_7$: | 45.93 | 4.71 | 2.98 |
| Found: | 46.46 | 4.72 | 2.80 |

EXAMPLE 3

3,5,6-Trichloro-2-pyridyloxyacetyl-1,2-(isopropylidene)-glycerol (Compound VI)

N,N'-carbonyldiimidazole (8.75 g, 0.054 mole) was added to 3,5,6-trichloro-2-pyridyloxyacetic acid (13.8 g, 0.054 mole) in dry tetrahydrofuran (120 ml) at room temperature with constant stirring. When evolution of carbon dioxide ceased, the mixture was treated with 1,2-isopropylidene glycerol (7.1 g, 0.054 mole) and stirred for an additional hour and then allowed to stand overnight. The progress of the reaction was followed by TLC.

The solid precipitate was removed by filtration and the filtrate concentrated on the rotary evaporator. The oily residue was taken up in dichloromethane (100 ml) and washed thoroughly with water. After drying with sodium sulphate, evaporation gave a pale, brown oil. This was eluted with benzene over a neutral alumina column to yield the product as a pale yellow oil (8.3 g, 41.5 percent).

Elemental Analysis

|  | C | H | N |
|---|---|---|---|
| Calculated for $C_{13}H_{22}Cl_3NO_7$: | 42.13 | 3.81 | 3.78 |
| Found: | 42.07 | 3.75 | 3.66 |

After a short period of standing, the oil crystallized out. Recrystallization from hexane yielded the title compound (6.9 g, 34.5 percent) as a white crystalline solid, m.p. 73°–74° C.

EXAMPLE 4

1-(3,5,6-Trichloro-2-pyridyloxyacetyl)-2,4-(methylene)-adonitol (Compound VIII)

N,N'Carbonyloiimidazole (3.47 g, 0.0195 mole) was added to 3,5,6-trichloro-2-pyridyloxyacetic acid (5.0 g, 0.0195 mole) in dry tetrahydrofuran (70 ml) at room temperature with constant stirring. When evolution of carbon dioxide ceased, the mixture was added dropwise to a solution of 2,4-methylene adonitol (3.2 g, 0.0195 mole) in dry tetrahydrofuran (70 ml). After stirring for an hour, the reaction was allowed to stand overnight.

The solid precipitate was removed by filtration, and the filtrate concentrated on a rotary evaporator. The oil residue was taken up in dichloromethane (100 ml) and washed thoroughly with water. After drying with sodium sulphate, evaporation gave a gum. This product was eluted with ethyl acetate and hexane mixtures (starting with 1:4 and ending with 100 percent ethyl acetate) over a silica column to yield the product as a white solid, m.p. 123.6° C. (7.0 g, 79.5 percent).

Elemental Analysis

|  | C | H | N |
|---|---|---|---|
| Calculated for $C_{13}H_{22}Cl_3NO_7$: | 38.78 | 3.51 | 3.48 |
| Found: | 38.99 | 3.47 | 3.54 |

EXAMPLES 5 TO 13

The following compounds were prepared in an analogous manner:

| Example No. | Name of Compound | M.pt. if solid (°C.) |
|---|---|---|
| 5 | (3,5,6-trichloro-2-pyridyloxy-acetyl)-2,3:4,5-di-O—(isopropylidene)xylitol; (Compound VII) | oil |
| 6 | (3,5,6-trichloro-2-pyridyloxy-acetyl)-1,3-(benzylidene)-glycerol; (Compound X) | 97.5 |
| 7 | (3,5,6-trichloro-2-pyridyloxy-acetyl)-1,2-(benzylidene)-glycerol; (Compound XI) | oil |
| 8 | (3,5,6-trichloro-2-pyridyloxy-acetyl)-1,2-(methylene)-glycerol; (Compound XII) | 120.5 |
| 9 | (3,5,6-trichloro-2-pyridyloxy-acetyl)-1,3:2,4-di-O—(methylene)-adonitol; (Compound XIII) | 126.2 |
| 10 | (3,5,6-trichloro-2-pyridyloxy-acetyl)-1,2-(butylidene)-glycerol; (Compound XIV) | oil |
| 11 | (3,5,6-trichloro-2-pyridyloxy-acetyl)-1,2-(cyclohexylidene)-glycerol; (Compound XV) | oil |
| 12 | (3,5,6-trichloro-2-pyridyloxy-acetyl)-2,3:4,5-di-O—(isopropylidene)-L-arabitol; (Compound XVI) | oil |
| 13 | bis-[1,4-(3,5,6-trichloro-2-pyridyloxyacetyl]-2,3-(isopropylidene)-threitol; Compound XVII | oil |

FORMULATION EXAMPLES

The following Examples A to C are illustrations of typical formulations in which the compounds of the invention may be utilized.

A. Wettable Powder (a)

40 percent by weight of active substance
25 percent by weight of clay minerals
20 percent by weight of colloidal silica
10 percent by weight of cellulose pitch
5 percent by weight of surfactant based on a mixture of the calcium salt of lignin-sulphonic acid and alkylphenol polyglycol ethers (b)

25 percent by weight of active substance
60 percent by weight of kaolin
10 percent by weight of colloidal silica
5 percent by weight of surfactant based on the sodium salt of N-methyl-N-oleyltaurine and the calcium salt of lignin-sulphonic acid (c)

10 percent by weight of active substance
60 percent by weight of clay minerals
15 percent by weight of cellulose pitch
10 percent by weight of surfactants based on the sodium salt of N-methyl-N-oleyltaurine and the calcium salt of lignin-sulphonic acid

B. Paste 45 percent by weight of active substance
5 percent by weight of sodium aluminum silicate
15 percent by weight of cetyl polyglycol ether with 8 moles of ethylene oxide
2 percent by weight of spindle oil
10 percent by weight of polyethylene glycol
23 percent by weight of water

C. Emulsion Concentrate (a)

25 percent by weight of active substance
15 percent by weight of cyclohexanone
55 percent by weight of xylene
5 percent by weight of a mixture of nonylphenyl polyoxyethylenes or calcium dodecylbenzenesulphonate (b)

10 percent by weight of active substance
6 percent by weight of cyclohexanone
36 percent by weight of xylene
12 percent by weight of a mixture of nonylphenyl polyoxyethylenes or calcium dodecylbenzenesulphonate
36 percent by weight of mineral oil having a high paraffin content.

The following examples illustrate possible uses of the compounds and mixtures according to the invention which were used in the form of the above-mentioned preparations.

EXAMPLE 14

Glasshouse tests were carried out to determine the herbicidal efficacy of a postemergence application of the esters of triclopyr prepared in Examples 1 to 13.

The esters of triclopyr in accordance with the invention were prepared as described hereinabove by coupling the corresponding free acid with the appropriate alditol derivative as described in Examples 1 to 4 in the presence of N,N'-carbonyldiimidazole. The chiral D- and L-ester herbicides were produced by using the corresponding D- and L-arabitol acetonides prepared from D- and L-alcohols. The esters were purified by column chromatography on neutral alumina.

The new compounds were characterized by infrared Spectroscopy, Nuclear Magnetic Resonance Spectroscopy and Elemental Analysis and had the structures given above.

Method

All plants were cultivated in the glasshouse, to a true 2–4 leaf stage, in a mixture of 70 percent peat, 20 percent sharp sand and 10 percent potting grit. Then they were placed in a cooler area to harden off, at temperatures ranging from 5° C. at night to 15° C. during the day.

Concentrates of the respective new compounds were made up as aqueous compositions in water utilizing 25 percent acetone and 0.25 percent of a surfactant (Triton X-100), to disperse the active ingredients (TRITON X-100 is a Trade Mark).

The concentrates were then further diluted with water containing 0.25 percent of Triton X-100, to produce sprayable formulations of the desired concentration.

All formulations were applied to the plants using a MARDRIVE overhead sprayer set at 30 psi, delivering 300 l/ha. Plants were returned to the glasshouse after treatment and were subjected to temperatures ranging between 15° C. at night to 20° C. during the day. The compounds were applied at rates of 960, 480 and 240 grams active ingredient (calculated as trichlopyr free acid) per hectare (g ai/ha).

Application of the formulations was made to the following plants postemergently.

| Weeds: | Crops: |
|---|---|
| Cleaver (*Galium aparine*) | Barley (Golden Promise) |
| Fat hen (*Chenopodium album*) | Wheat (Norman) |
| Red Dead nettle (*Lamium purpureum*) | |
| Pansy (*Viola arvensis*) | |

Assessments
A 0–5 scale was used to assess all tests:
0 = Normal healthy plants
5 = Dead Efficacy results at indicated times and application rates as summarized in Table 1.

TABLE 1

Activity Assessment of Arabitol Derivative Esters

| Compound No. | Rate g/ha | Cleaver Days | | | Red Dead Nettle Days | | | Pansy Days | | | Fat hen Days | | | Wheat Days | | | Barley Days | | |
|---|---|---|---|---|---|---|---|---|---|---|---|---|---|---|---|---|---|---|---|
| | | 4 | 13 | 19 | 4 | 13 | 19 | 4 | 13 | 19 | 4 | 13 | 19 | 4 | 13 | 19 | 4 | 13 | 19 |
| V | 960 | 3 | 3 | 1 | 3 | 4 | 4 | 3 | 3 | 3 | 4 | 4 | 4 | 0 | 0 | — | 0 | 0 | — |
| | 480 | 3 | 2 | 0 | 3 | 3 | 4 | 3 | 3 | 3 | 4 | 4 | 4 | 0 | 0 | — | 0 | 0 | — |
| | 240 | 2 | 2 | 0 | 2 | 3 | 3 | 3 | 3 | 2 | 4 | 4 | 4 | 0 | 0 | — | 0 | 0 | — |
| VI | 960 | 2 | 0 | 0 | 2 | 2 | 4 | 1 | 3 | 2 | 4 | 4 | 4 | 0 | 0 | 0 | 0 | 0 | 0 |
| | 480 | 1 | 0 | 0 | 0 | 1 | 2 | 1 | 2 | 1 | 4 | 4 | 4 | 0 | 0 | 0 | 0 | 0 | 0 |
| | 240 | 0 | 0 | 0 | 0 | 1 | 2 | 0 | 2 | 0 | 4 | 4 | 4 | 0 | 0 | 0 | 0 | 0 | 0 |
| VII | 960 | 0 | 0 | 0 | 0 | 2 | 3 | 1 | 1 | 0 | 3 | 4 | 4 | 0 | 0 | 0 | 0 | 0 | 0 |
| | 480 | 0 | 0 | 0 | 0 | 2 | 2 | 1 | 1 | 0 | 3 | 3 | 4 | 0 | 0 | 0 | 0 | 0 | 0 |
| | 240 | 0 | 0 | 0 | 0 | 2 | 2 | 1 | 1 | 0 | 2 | 3 | 4 | 0 | 0 | 0 | 0 | 0 | 0 |
| VIII | 960 | 1 | 2 | 2 | 1 | 2 | 2 | 2 | 2 | 2 | 3 | 4 | 4 | 0 | 0 | 0 | 2 | 1 | 1 |
| | 480 | — | — | — | — | — | — | 2 | 2 | 1 | 3 | 4 | 3 | — | — | — | 2 | 1 | 1 |
| | 240 | — | — | — | — | — | — | 2 | 2 | 1 | 2 | 3 | 3 | — | — | — | 2 | 1 | 1 |
| IX | 960 | 0 | 0 | 0 | 0 | 0 | 0 | 1 | 2 | 2 | 3 | 4 | 3 | 0 | 0 | 0 | 2 | 1 | 0 |
| | 480 | — | — | — | — | — | — | 1 | 1 | 1 | 2 | 3 | 2 | — | — | — | 1 | 1 | 0 |
| | 240 | — | — | — | — | — | — | 0 | 0 | 0 | 2 | 3 | 2 | — | — | — | 1 | 1 | 0 |
| X | 960 | 2 | 2 | 3 | 1 | 0 | 1 | 0 | 1 | 1 | 2 | 3 | 3 | 0 | 0 | 0 | 2 | 0 | 0 |
| | 480 | — | — | — | 1 | 0 | 0 | 0 | 1 | 0 | 2 | 3 | 3 | — | — | — | 1 | 0 | 0 |
| | 240 | — | — | — | 1 | 0 | 0 | 0 | 1 | 0 | 2 | 3 | 3 | — | — | — | 1 | 0 | 0 |
| XI | 960 | 2 | 3 | 4 | 2 | 3 | 3 | 3 | 2 | 3 | 3 | 3 | 3 | 0 | 0 | 0 | 3 | 3 | 3 |
| | 480 | — | — | — | — | — | — | — | — | — | — | — | — | — | — | — | — | — | — |
| | 240 | — | — | — | — | — | — | — | — | — | — | — | — | — | — | — | — | — | — |
| XII | 960 | 2 | 0 | 0 | 1 | 3 | 3 | 1 | 3 | 2 | 2 | 3 | 3 | 0 | 0 | 0 | 0 | 1 | 1 |
| | 480 | 2 | 0 | 0 | 0 | 2 | 2 | 1 | 1 | 0 | 2 | 3 | 3 | 0 | 0 | 0 | 0 | 0 | 0 |
| | 240 | 1 | 0 | 0 | 0 | 2 | 2 | 1 | 1 | 0 | 2 | 3 | 3 | 0 | 0 | 0 | 0 | 0 | 0 |
| XIII | 960 | 1 | 1 | 2 | 0 | 0 | 0 | 1 | 0 | 1 | 3 | 3 | 2 | 0 | 0 | 0 | 1 | 0 | 0 |
| | 480 | — | — | — | — | — | — | 1 | 0 | 0 | 2 | 2 | 2 | — | — | — | 1 | 0 | 0 |
| | 240 | — | — | — | — | — | — | 0 | 0 | 0 | 2 | 2 | 0 | — | — | — | 0 | 0 | 0 |
| XIV | 960 | 2 | 3 | 4 | — | — | — | 3 | 2 | 4 | 3 | 3 | 3 | 0 | 0 | 0 | 3 | 3 | 4 |
| | 80 | 1 | 2 | 2 | — | — | — | 3 | 2 | 4 | 3 | 3 | 3 | 0 | 0 | 0 | 2 | 3 | 3 |
| XV | 960 | 2 | 3 | 4 | — | — | — | 3 | 3 | 4 | 3 | 4 | 4 | 0 | 0 | 0 | 3 | 3 | 3 |
| | 480 | 2 | 3 | 3 | — | — | — | 3 | 3 | 4 | 3 | 3 | 3 | 0 | 0 | 0 | 3 | 3 | 3 |
| XVI | 960 | 3 | 3 | 2 | 2 | 4 | 4 | 3 | 3 | 4 | 4 | 5 | 0 | 0 | — | 0 | 0 | — | |
| | 480 | 2 | 3 | 2 | 3 | 4 | 4 | 3 | 2 | 2 | 4 | 4 | 5 | 0 | 0 | — | 0 | 0 | — |
| | 240 | 2 | 2 | 0 | 3 | 3 | 3 | 2 | 2 | 0 | 4 | 4 | 5 | 0 | 0 | — | 0 | 0 | — |
| XVII | 960 | 1 | 1 | 1 | — | — | — | 2 | 0 | 1 | 3 | 3 | 3 | 0 | 0 | 0 | 2 | 2 | 2 |
| | 480 | 1 | 0 | 1 | — | — | — | 2 | 0 | 1 | 3 | 3 | 3 | 0 | 0 | 0 | 2 | 2 | 1 |

TABLE 1-continued

| Compound No. | Rate g/ha | Cleaver Days 4 | 13 | 19 | Red Dead Nettle Days 4 | 13 | 19 | Pansy Days 4 | 13 | 19 | Fat hen Days 4 | 13 | 19 | Wheat Days 4 | 13 | 19 | Barley Days 4 | 13 | 19 |
|---|---|---|---|---|---|---|---|---|---|---|---|---|---|---|---|---|---|---|---|
| Control | — | 0 | 0 | 0 | 0 | 0 | 0 | 0 | 0 | 0 | 0 | 0 | 0 | 0 | 0 | 0 | 0 | 0 | 0 |

Assessment Scale 0–5:
0 = Normal healthy plants;
5 = dead

EXAMPLE 15

Various of the alditol ester according to the invention were tested for their volatile vapor effects on adjacent sensitive crops.

A wind tunnel was prepared using a glasshouse constructed of transparent rigid sheets secured to a tubular aluminum frame 0.43 m high, 0,84 m wide and 3.05 m in length.

An airflow was introduced into one end of the tunnel using a Secomak (Model 573) fan giving an airflow of ¾ M.P.H. from a manifold and vented to the atmosphere at the opposite end of the tunnel.

Test compounds were sprayed over a field target containing plants representative of plants to be treated in the field at normal field rates and volumes (substantially 960 g/ha calculated as trichlopyr free acid). The target was allowed to dry and was then introduced into the upwind end of the tunnel. Air was passed over the target for a period of 24 hours and vented to the atmosphere outside the glasshouse.

Various sensitive plants (cotton, barley, pinto beans, and rape) were grown at varying distances downwind of the target over the 24 hour period.

After 24 hours the sensitive plants were removed from the tunnel and grown on a glasshouse bench for a further period of 14 days.

Plants exposed at distances of 0, 1, 2, 3, 4 5, 6 and 7 feet (0, 0.3, 0.6, 0.9, 1.2, 1.5, 1.8 and 2.1 meters) from the target were assessed visually immediately after removal from the tunnel, on a scale of 0 to 5, where 0=normal healthy plants, and 5=dead.

The results are shown in Table 2. Further observation of the plants over the 14-day period after removal from the tunnel showed no significant change in their score from those obtained immediately after their removal from the tunnel.

TABLE 2

| Compound No. | Cotton Distance in Feet 0 1 2 3 4 5 6 7 | Barley Distance in Feet 0 1 2 3 4 5 6 7 | Pinto Beans Distance in Feet 0 1 2 3 4 5 6 7 | Rape Distance in Feet 0 1 2 3 4 5 6 7 |
|---|---|---|---|---|
| VI | 0 0 0 0 0 0 0 0 | 0 0 0 0 0 0 0 0 | 0 0 0 0 0 0 0 0 | 0 0 0 0 0 0 0 0 |
| VII | 0 0 0 0 0 0 0 0 | 0 0 0 0 0 0 0 0 | 0 0 0 0 0 0 0 0 | 0 0 0 0 0 0 0 0 |
| XII | 0 0 0 0 0 0 0 0 | 0 0 0 0 0 0 0 0 | 0 0 0 0 0 0 0 0 | 0 0 0 0 0 0 0 0 |
| XVI | 0 0 0 0 0 0 0 0 | 0 0 0 0 0 0 0 0 | 0 0 0 0 0 0 0 0 | 0 0 0 0 0 0 0 0 |
| Control | 0 0 0 0 0 0 0 0 | 0 0 0 0 0 0 0 0 | 0 0 0 0 0 0 0 0 | 0 0 0 0 0 0 0 0 |

Volatility Assessments of Arabitol Derivative Esters

Assessment Scale 0–5:
0 = Normal healthy plants;
5 = dead

EXAMPLE 16

Representative compositions of the present invention were evaluated to determine their selectivity to wheat in postemergent operations.

Aqueous dispersions were prepared by admixing predetermined amounts of one of the hereinafter set forth compounds, dissolved in a predetermined amount of an inert solvent with a predetermined quantity of water and a predetermined amount of a surfactant to give aqueous dispersions of one of the compounds as the sole toxicant.

Plant seeds of predetermined plant species were planted in beds of good agricultural soil and grown in a greenhouse. After the plants had emerged and had grown to the four leaf stage, the plants were sprayed to runoff with one of the above-prepared compositions at treating rates. Other beds of the plants were sprayed with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds and the percent postemergent control are set forth in Table 3.

TABLE 3

Wheat Selectivity of Arabitol Derivative Esters

Percent Kill and Control of Indicated Plant Species at Indicated Treating Rate

| Compound No. | Treating Rate g/ha | Wheat | Velvet Leaf | Morning Glory | Jimson Weed | Cocklebur |
|---|---|---|---|---|---|---|
| V | 1290 | 0 | 40 | 100 | NT | 100 |
|   | 640 | 0 | 40 | 100 | 100 | 70 |
| VI | 1290 | 0 | 75 | 100 | NT | 100 |
|   | 640 | 0 | 55 | 100 | 95 | 95 |
| VII | 1290 | 0 | 80 | 100 | 95 | NT |
|   | 640 | 0 | 80 | 100 | 85 | NT |
| VIII | 1290 | 20 | 60 | 100 | 98 | 98 |

TABLE 3-continued

Wheat Selectivity of Arabitol Derivative Esters

| Compound No. | Treating Rate g/ha | Percent Kill and Control of Indicated Plant Species at Indicated Treating Rate | | | | |
|---|---|---|---|---|---|---|
| | | Wheat | Velvet Leaf | Morning Glory | Jimson Weed | Cocklebur |
| | 640 | 0 | 70 | 100 | 40 | 90 |
| X | 1290 | 20 | 100 | 100 | 100 | 98 |
| | 640 | 0 | 100 | 100 | 100 | 95 |
| XII | 1290 | 0 | NT | 100 | 90 | NT |
| | 640 | 0 | 70 | 100 | 50 | NT |
| XIII | 1290 | 35 | 60 | 100 | 100 | 90 |
| | 640 | 20 | 60 | 100 | 90 | 80 |
| Control | — | 0 | 0 | 0 | 0 | 0 |

EXAMPLE 17

Representative compositions of the present invention were evaluated to determine their selectivity to rice in postemergent operations.

Aqueous disperesions were prepared by admixing predetermined amounts of one of the hereinafter set forth compounds, dissolved in a predetermined amount of an inert solvent with a predetermined quantity of water and a predetermined amount of a surfactant to give aqueous dispersions of one of the compounds as the sole toxicant.

Plant seeds of predetermined plant species were planted in beds of good agricultural soil and grown in a greenhouse. After the plants had emerged and had grown to the four leaf stage, the plants were sprayed to runoff with one of the above-prepared compositions at treating rates. Other beds of the plants were sprayed with a water-surfactant mixture, containing no active compound, to serve as controls. After treatment, the beds were maintained for two weeks under greenhouse conditions conducive for good plant growth. At the end of the period, the beds were examined to determine the amount of kill and control. The specific plant species, test compounds and the percent postemergent control are set forth below in Table 4.

TABLE 4

Rice Selectivity of Arabitol Derivative Esters

| Compound No. | Treating Rate g/ha | Percent Kill and Control of Indicated Plant Species at Indicated Treating Rate | | | | |
|---|---|---|---|---|---|---|
| | | Rice | Velvet Leaf | Morning Glory | Jimson Weed | Cocklebur |
| VI | 1290 | 35 | 75 | 100 | NT | 100 |
| | 640 | 0 | 55 | 100 | 95 | 95 |
| VII | 1290 | 0 | 80 | 100 | 95 | NT |
| | 640 | 0 | 80 | 100 | 85 | NT |
| VIII | 1290 | 40 | 60 | 100 | 98 | 98 |
| | 640 | 0 | 70 | 100 | 40 | 90 |
| XII | 1290 | 30 | NT | 100 | 90 | NT |
| | 640 | 0 | 70 | 100 | 50 | NT |
| XIII | 1290 | 30 | 60 | 100 | 100 | 90 |
| | 640 | 0 | 60 | 100 | 90 | 80 |
| Control | — | 0 | 0 | 0 | 0 | 0 |

We claim:

1. A compound corresponding to one of the general formula

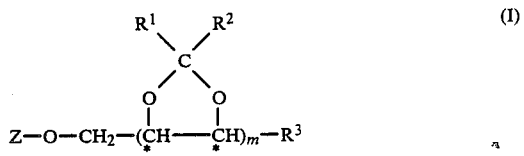

wherein
Z represents

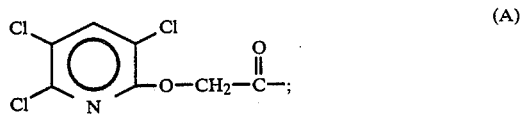

$R^1$ and $R^2$ are each independently any sterically compatible combination of H, a $C_1$–$C_6$ straight chain or branched alkyl group, a $C_3$–$C_6$ cycloalkyl group, or phenyl;

$R^1$ and $R^2$ taken together represent a divalent polymethylene group $-(CH_2)_n-$, thereby forming a carbocyclic ring having $n+1$ carbon atoms wherein n is 3, 4, 5 or 6;

$R^3$ is H or a group of the formula:

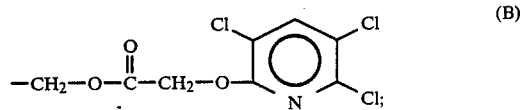

$R^4$ is H, $CH_2OH$ or a group of formula B; and
m is 1 or 2.

2. A compound as defined in claim 1 wherein $R^1$ and $R^2$ are each independently H, methyl or phenyl.

3. A compound as defined in claim 1 wherein $R^1$ and $R^2$ are different.

4. A compound as defined in claim 2 wherein $R^1$ and $R^2$ are the same.

5. A compound as defined in claim 4 wherein $R^1$ and $R^2$ are each hydrogen or methyl.

6. A compound as defined in claim 5 wherein $R^1$ and $R^2$ are each hydrogen.

7. A compound as defined in claim 5 wherein $R^1$ and $R^2$ are each methyl.

8. The compound as defined in claim 7 which is (3,5,6-trichloro-2-pyridyloxyacetyl)2,3:4,5-di-O-(isopropylidene)-D-arabitol.

9. The compound as defined in claim 7 which is (3,5,6-trichloro-2-pyridyloxyacetyl)1,2-(isopropylidene)-glycerol.

10. The compound as defined in claim 7 which is (3,5,6-trichloro-2-pyridyloxyacetyl)2,3:4,5-di-O-(isopropylidene)-xylitol.

11. The compound as defined in claim 3 which is (3,5,6-trichloro-2-pyridyloxyacetyl)1,2-(benzylidene)-glycerol.

12. The compound as defined in claim 6 which is (3,5,6-trichloro-2-pyridyloxyacetyl)1,2-methylene glycerol.

13. The compound as defined in claim 3 which is (3,5,6-trichloro-2-pyridyloxyacetyl)1,2-(butylidene)-glycerol.

14. The compound as defined in claim 1 which is (3,5,6-trichloro-2-pyridyloxyacetyl)1,2-(cyclohexylidene)-glycerol.

15. The compound as defined in claim 7 which is (3,5,6-trichloro-2-pyridyloxyacetyl)2,3:4,5-di-O-(isopropylidene)-L-arabitol.

16. The compound as defined in claim 7 which is bis-[(3,5,6-trichloro-2-pyridyloxyacetyl)]2,3-(isopropylidene)-threitol.

17. A herbicidal composition which contains as the active component an alditol derivative ester of triclopyr in intimate admixture with an inert carrier therefor and said active component is a compound corresponding to one of the general formula $$\begin{array}{c} R^1 \diagdown \diagup R^2 \\ C \\ O \quad O \\ | \quad | \\ Z-O-CH_2-(CH\underset{*}{\longrightarrow}CH)_m-R^3, \end{array} \quad (I)$$

wherein
Z represents $$\begin{array}{c} Cl \diagdown \diagup Cl \\ \diagup \diagdown \\ Cl \diagup N \diagdown O-CH_2-\underset{\parallel}{C}-; \\ O \end{array} \quad (A)$$

$R^1$ and $R^2$ are each independently any sterically compatible combination of H, a $C_1-C_6$ straight chain or branched alkyl group, a $C_3-C_6$ cycloalkyl group, or phenyl;

$R^1$ and $R^2$ taken together represent a divalent polymethylene group $(CH_2)_n$, thereby forming a carbocyclic ring having n+1 carbon atoms wherein n is 3, 4, 5 or 6;

$R^3$ is H or a group of the formula:

$$\begin{array}{c} Cl \diagdown \diagup Cl \\ -CH_2-O-\underset{\parallel}{C}-CH_2-O \diagup N \diagdown Cl; \\ O \end{array} \quad (B)$$

$R^1$ is H, $CH_2OH$ or a group of formula B; and m is 1 or 2.

18. A composition as defined in claim 2 wherein $R^1$ and $R^2$ are each independently H, methyl or phenyl.

19. A composition as defined in claim 18 wherein $R^1$ and $R^2$ are different.

20. A composition as defined in claim 18 wherein $R^1$ and $R^2$ are the same.

21. A composition as defined in claim 20 wherein $R^1$ and $R^2$ are each hydrogen or methyl.

22. A composition as defined in claim 21 wherein $R^1$ and $R^2$ are each hydrogen.

23. A composition as defined in claim 20 wherein $R^1$ and $R^2$ are each methyl.

24. The composition as defined in claim 23 wherein the compound is (3,5,6-trichloro-2-pyridyloxyacetyl)2,3:4,5-di-O-(isopropylidene)-D-arabitol.

25. The composition as defined in claim 23 wherein the compound is (3,5,6-trichloro-2-pyridyloxyacetyl)1,2-(isopropylidene)-glycerol.

26. The composition as defined in claim 23 wherein the compound is (3,5,6-trichloro-2-pyridyloxyacetyl)2,3:4,5-di-O-(isopropylidene)-xylitol.

27. A method for the postemergent kill and control of weeds which comprises applying to said weeds a herbicidally effective amount of a composition containing as the active component an alditol derivative ester of triclopyr in intimate admixture with an inert carrier therefor and said active component is a compound corresponding to one of the general formula $$\begin{array}{c} R^1 \diagdown \diagup R^2 \\ C \\ O \quad O \\ | \quad | \\ Z-O-CH_2-(CH\underset{*}{\longrightarrow}CH)_m-R^3, \end{array} \quad (I)$$

wherein
Z represents $$\begin{array}{c} Cl \diagdown \diagup Cl \\ \diagup \diagdown \\ Cl \diagup N \diagdown O-CH_2-\underset{\parallel}{C}-; \\ O \end{array} \quad (A)$$

$R^4$ is H, $CH_2OH$ or a group of formula B; and m is 1 or 2.

28. A method as defined in claim 27 wherein $R^1$ and $R^2$ are each independently H, methyl or phenyl.

29. A method as defined in claim 28 wherein $R^1$ and $R^2$ are different.

30. A method as defined in claim 28 wherein $R^1$ and $R^2$ are the same.

31. A method as defined in claim 30 wherein $R^1$ and $R^2$ are each hydrogen or methyl.

32. A method as defined in claim 31 wherein $R^1$ and $R^2$ are each hydrogen.

33. A method as defined in claim 28 wherein $R^1$ and $R^2$ are each methyl.

34. The method as defined in claim 33 wherein the compound is (3,5,6-trichloro-2-pyridyloxyacetyl)2,3:4,5-di-O-(isopropylidene)-D-arabitol.

35. The method as defined in claim 33 wherein the compound is (3,5,6-trichloro-pyridyloxyacetyl)1,2-(isopropylidene)-glycerol.

36. The method as defined in claim 33 wherein the compound is (3,5,6-trichloro-2-pyridyloxyacetyl)2,3:4,5-di-O-(isopropylidene)-xylitol.

37. A composition as defined in claim 19 wherein the compound is (3,5,6-trichloro-2-pyridyloxyacetyl)1,2-(benzylidene)-glycerol.

38. A composition as defined in claim 22 wherein the compound is (3,5,6-trichloro-2-pyridyloxyacetyl)1,2-methylene glycerol.

39. A composition as defined in claim 19 wherein the compound is (3,5,6-trichloro-2-pyridyloxyacetyl)1,2-(butylidene)-glycerol.

40. A composition as defined in claim 17 wherein the compound is (3,5,6-trichloro-2-pyridyloxyacetyl)1,2-(cyclohexylidene)-glycerol.

41. A composition as defined in claim 22 wherein the compound is (3,5,6-trichloro-2-pyridyloxyacetyl)2,3:4,5-di-O-(isopropylidene)-L-arabitol.

42. A composition as defined in claim 22 wherein the compound is bis-[(3,5,6-trichloro-2-pyridyloxyacetyl)]2,3-(isopropylidene)-threitol.

43. A method as defined in claim 29 wherein the compound is (3,5,6-trichloro-2-pyridyloxyacetyl)1,2-(benzylidene)-glycerol.

44. A method as defined in claim 32 wherein the compound is (3,5,6-trichloro-2-pyridyloxyacetyl)1,2-methylene glycerol.

45. A method as defined in claim 29 wherein the compound is (3,5,6-trichloro-2-pyridyloxyacetyl)1,2-(butylidene)-glycerol.

46. A method as defined in claim 27 wherein the compound is (3,5,6-trichloro-2-pyridyloxyacetyl)1,2-(cyclohexylidene)-glycerol.

47. A method as defined in claim 32 wherein the compound is (3,5,6-trichloro-2-pyridyloxyacetyl)2,3:4,5-di-O-(isopropylidene)-L-arabitol.

48. A method as defined in claim 32 wherein the compound is bis-[(3,5,6-trichloro-2-pyridyloxyacetyl)]2,3-(isopropylidene)-threitol.

* * * * *